(12) United States Patent
Warden

(10) Patent No.: US 12,636,464 B2
(45) Date of Patent: May 26, 2026

(54) PISTONING PREVENTION SYSTEM (PPS) OF INDWELLING FOLEY CATHETERS

(71) Applicant: John Bradley Warden, Chickasha, OK (US)

(72) Inventor: John Bradley Warden, Chickasha, OK (US)

( * ) Notice: Subject to any disclaimer, the term of this patent is extended or adjusted under 35 U.S.C. 154(b) by 1034 days.

(21) Appl. No.: 16/926,578

(22) Filed: Jul. 10, 2020

(65) Prior Publication Data

US 2021/0008337 A1 Jan. 14, 2021

Related U.S. Application Data

(60) Provisional application No. 62/873,085, filed on Jul. 11, 2019.

(51) Int. Cl.
  *A61M 25/00* (2006.01)
  *A61M 25/04* (2006.01)
(52) U.S. Cl.
  CPC .... *A61M 25/0017* (2013.01); *A61M 25/0012* (2013.01); *A61M 25/0043* (2013.01); *A61M 25/04* (2013.01)
(58) Field of Classification Search
  CPC .............. A61M 25/04; A61M 25/0012; A61M 25/0017; A61M 25/0043; A61M 25/10; A61M 25/0054; A61M 25/005; A61M 25/0144; A61M 25/008; A61M 25/0053; A61M 2025/0063; B29K 2105/06; B29K 2105/08
  See application file for complete search history.

(56) References Cited

U.S. PATENT DOCUMENTS

| | | | | | |
|---|---|---|---|---|---|
| 4,823,805 | A | * | 4/1989 | Wojcik ..................... | A61B 5/01 604/524 |
| 6,184,298 | B1 | * | 2/2001 | Lee ........................... | B32B 7/12 428/476.3 |
| 2014/0148673 | A1 | * | 5/2014 | Bogusky ........... | A61M 25/0052 604/95.04 |
| 2014/0371672 | A1 | * | 12/2014 | Pinchuk ............ | A61M 25/0017 604/99.02 |
| 2020/0155311 | A1 | * | 5/2020 | Vidlund ................ | A61F 2/2436 |

* cited by examiner

*Primary Examiner* — Rebecca E Eisenberg
*Assistant Examiner* — Timothy L Flynn
(74) *Attorney, Agent, or Firm* — Chen-Chi Lin

(57) ABSTRACT

A pistoning prevention system (PPS) that will improve catheter associated urinary tract infection rates of an indwelling Foley catheter while maintaining reliability, comfort, & safety. With the PPS incorporated within a Foley catheter during manufacturing it will eliminate the excess stretch along a specific length of a Foley catheter that resides within the patient's urethra. The excessive amount and ease of stretch is responsible for the pistoning action of an indwelling Foley catheter moving in and out of the urethra. This action is responsible for the retrograde movement of bacteria outside the body & into the urethra, bladder, & kidneys increasing preventable infections. With much prevention work globally, the pistoning action of a Foley catheter is now known to be partially or wholly to blame for the attributed $340 million spent in the U.S. on healthcare costs & 13,000 associated deaths making this an immediate global patient safety emergency.

18 Claims, 1 Drawing Sheet

PISTONING PREVENTION SYSTEM (PPS) OF INDWELLING FOLEY CATHETERS

CROSS REFERENCE TO RELATED APPLICATIONS

The present patent application claims benefit of U.S. Provisional Application Ser. No. 62/873,085 filed on 11 Jul. 2019, incorporated herein by reference.

TECHNICAL FIELD

This invention relates to indwelling Foley catheters, and more specifically, to a device that prevents excessive stretch of the Foley catheter where the Foley catheter resides within the urethra.

BACKGROUND

A Foley catheter is a hollow tube inserted through the urethra into the bladder to empty it of urine. A catheter is commonly used for medical purposes such as sickness, palliative care, incontinence in a patient with pressure ulcers & perineal wounds, bladder injury, or recent surgery involving structures contiguous with the bladder or urinary tract. The most distal part of the urinary tract is the urethral meatus and the most proximal is the bladder. The insertion of an indwelling Foley catheter starts at the meatus and ends in the bladder, whether male or female. This process is known as catheterization. It is an aseptic procedure performed by qualified medical staff.

Unfortunately, many patients develop a urinary-tract infection (UTI) after catheterization; referred to as a catheter-associated-urinary-tract infection (CAUTI). This is one of the leading healthcare-associated infections (HAI's) in the United States. For each day a Foley catheter is used a person has a 3-7% chance of acquiring a UTI and at day 30, it's a 100%. Some technology and several strategies have been implemented over the last decade to reduce this risk with only one showing consistent improvement. That strategy showing improvement is to decrease the device utilization in the healthcare setting. This is where certain catheterization requirements are checked to make sure the device is absolutely necessary for the patient. Therefore, what is needed is a better way to reduce the quantity and incidence of CAUTI for those patient's requiring the use of an indwelling Foley catheter.

Despite the focus on sterile insertion techniques, catheter coatings to negate bacterial growth, anti-reflux valves, catheter cleaning care and maintenance, CAUTI rates are not decreasing. These infections are becoming more alarming as we are seeing an ever increasing rate of CAUTI's associated with multi-drug-resistant-organisms (MDRO). These types of organisms make it more difficult to treat and in some instances, an incurable infection. Therefore, what is needed is a way to reduce and prevent the incidence of CAUTI's.

SUMMARY

Despite all the strategies and technologies showing limited infection risk reduction except for the decrease in device utilization, it is time to look at improving the Foley catheter itself. Let's discuss the actual technical problem. It's known that germs migrate on the extraluminal (outside) surface of the catheter and travel toward and infect the urethra, bladder and kidneys. Germs will travel this route because it is not closed or sealed.

It is extremely difficult to completely prevent the bacterial migration, only to delay it. Delaying the migration will result in less infections, less lives lost, less healthcare costs.

Current aseptic insertion techniques, catheter cleaning and care interventions, catheter anti-reflux valves, catheter anti-microbial coatings, catheter material selections all have shown little to no improvement in catheter related infection rates. The reason is these interventions cannot overcome the inadvertent stretching & pistoning action that causes a retrograde pumping movement of bacteria along the extraluminal surface. The number of bacteria introduced repeatedly is just too great for natural defenses and immunity to overcome.

This inadvertent pistoning is an action that can be caused by patient movement, inadvertent tugging or manual manipulation, and even during catheter care.

The pistoning action is due to a catheter being made of a stretchable latex or silicone which allows for significant longitudinal stretch, much like a rubber band, of up to >350% of its length. This physical property of the catheter material promotes and exacerbates the pistoning action where the catheter can stretch significantly out through the urethra, past the meatus and then return back again.

Currently there is not a sure way to reduce this inadvertent pistoning action, only to try and minimize it with current securing leg attachment devices. However, in many cases this can make the pistoning action worse with possible misplaced securing device locations and entanglement of the catheter to the securing device.

To address the above-discussed issues, described herein is the PPS. The PPS a device when placed internally during the manufacturing of an indwelling Foley catheter, will greatly decrease stretch of the catheter along the PPS' length. This stretch reduction in turn will reduce pistoning and subsequent accelerated transfer of microorganisms into the urinary system. By decreasing the rate of microorganism transfer will reduce the quantity and incidence of CAUTI.

The advantage in the invention of the PPS device is it is a reliable way in pistoning prevention as the PPS device is encased within the catheter body alongside the hollow tube. In examples of the present disclosure, the device is adapted to be placed within the rubber mold of the Foley catheter during manufacture. It almost completely eliminates the pistoning action from latex or silicone stretch. It does this by binding the latex or silicone material of the catheter to the PPS and anchoring eyelets internally. This process decreases only the longitudinal stretch property of the latex or silicone while maintaining complete lateral flexibility, comfort, & safety.

The PPS only needs placed within the silicone or latex Foley catheter where it resides in the urethra for a length of 2 inches or more and as close to the balloon as possible. This will allow for significant external stretch distally of the PPS should the catheter get bound or caught on something. In essence, it would not pose any risk by decreasing stretch of the catheter within the urethra. However, having excess stretch in a significant vulnerable area, such as the urethra, poses a very high risk of infection.

Along with the advantages mentioned previously and by decreasing longitudinal stretch of the catheter along where it resides in the urethra, some key advantages are: (1) It will not significantly limit lateral flexibility. It will continue to allow the catheter to conform easily to the shape of the male and female urethra upon insertion and will add comfort for long term use by; (2) preventing friction between the extraluminal catheter surface and the urethral lining by reducing the pistoning action; (3) It will significantly increase comfort by decreasing bacterial contact and migration across the urethral mucosal lining which in turn; (4) decreases infections by limiting the pistoning assistance of bacterial migration into the urethral mucous membrane, bladder, and kidneys.

DETAILED DESCRIPTION OF EMBODIMENT—FIGS. 1-4

Figure 1:
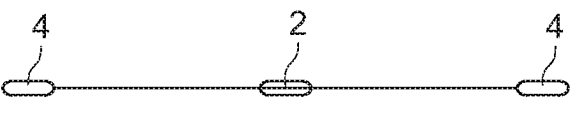
FIG. 1 shows an aspect of the PPS from end to end.

An embodiment of the present invention is illustrated in FIG. 1. The PPS has a cord body 2 that consists of a flexible material that can be repeatedly flexed without fracturing or significant stretching longitudinally beyond its original length. An anchoring eyelet of the same or differing material is placed on each end and in the middle or similar array. 4. The eyelets can also be made of a different cord shape or material than the PPS body. In the preferred embodiment, the PPS body and eyelets are made of a flexible material that can be repeatedly bent without stretching or fracturing, such as polyethylene, polypropylene, nylon, various impregnated or laminated fibrous materials and various plasticized materials. Material selection, gauge or thickness, and shape can be adjusted based on achieving a desired flexibility to strength ratio which will be dependent on the physical properties of the material(s) used.

Figure 2:
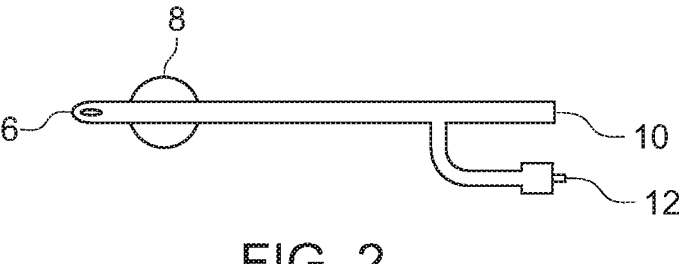
FIG. 2 shows a representation of a typical double lumen indwelling Foley catheter.

In FIG. 2 is the typical representation of an indwelling Foley catheter. At the tip 6 you have the drainage eyelet. The anchoring balloon 8 keeps the Foley in place. The drainage port 10 is connected to the drainage bag. Once Foley is inserted, the balloon 8 is inflated through balloon port 12.

Figure 3:
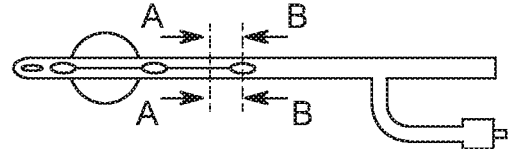
FIG. 3 shows a representation of a longitudinal section of a typical indwelling Foley catheter with corresponding placement of the PPS. It also denotes the location of two cross sections located in FIG. 4.

FIG. 3 shows the preferred embodiment of the PPS system within the Foley catheter with 2 cross sectional views located at A-A and B-B. The anchoring eyelets should be placed on either side of balloon with cord body running through the non-expanding material below the balloon. The $3^{rd}$ or last anchoring eyelet, closest to drainage port, can be placed at varying distances but should not be greater than the urethra length.

Figure 4:
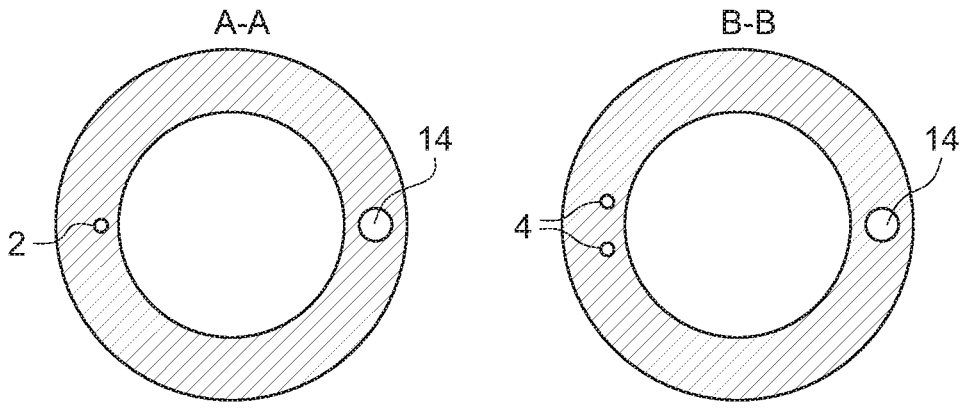
FIG. 4 shows a representation of a cross section view of a typical indwelling Foley catheter with corresponding placement of the PPS.

FIG. 4 illustrates the cross sectional views of the PPS within the catheter 2 & 4. The balloon filling channel 14 runs between the balloon 8 and the balloon port 12.

The invention claimed is:

1. A device to be placed in an indwelling Foley catheter, the device comprising
   a cord body;
   a first anchoring eyelet attached to a first end of the cord body;
   a second anchoring eyelet attached to a second end of the cord body; and
   an additional anchoring eyelet attached to a middle portion of the cord body;
wherein the second end of cord body is opposite to the first end of the cord body.

2. The device as recited in claim 1, wherein the cord body, the first anchoring eyelet, and the second anchoring eyelet are made of a same flexible non-stretch material.

3. The device as recited in claim 1, wherein the cord body, the first anchoring eyelet, and the second anchoring eyelet are made from braided polymers.

4. The device as recited in claim 1, wherein the device is adapted to be placed within a rubber mold of the Foley catheter during manufacture.

5. The device as recited in claim 1, wherein the indwelling Foley catheter comprises
   a balloon port; and
   a balloon inflated through the balloon port;
   wherein the balloon keeps the indwelling Foley catheter in place;
   wherein an entirety of the first anchoring eyelet is positioned on a first side of the balloon;
   wherein a majority portion of the second anchoring eyelet is positioned on a second side of the balloon; and
   wherein the second side is opposite to the first side.

6. The device as recited in claim 1, wherein the cord body, the first anchoring eyelet, and the second anchoring eyelet are made from silk, polymer, silicone, polyurethane, plastic, polyethylene, polypropylene, nylon, or laminated fibrous materials.

7. The device as recited in claim 1, wherein the indwelling Foley catheter further comprises:
   a non-expanding material below a balloon;
   wherein the cord body of the device runs through the non-expanding material of the indwelling Foley catheter.

8. The device as recited in claim 7, wherein the indwelling Foley catheter comprises
   a balloon port; and
   a balloon inflated through the balloon port;
   wherein the balloon keeps the indwelling Foley catheter in place;
   wherein a centroid of the first anchoring eyelet is positioned on a first side of the balloon;
   wherein a centroid of the second anchoring eyelet is positioned on a second side of the balloon; and
   wherein the second side is opposite to the first side.

9. The device as recited in claim 1, wherein a length of the cord body is shorter than a distance between a centroid of the first anchoring eyelet and a centroid of the second anchoring eyelet.

10. The device as recited in claim 9, wherein the first end of the cord body is directly attached to an exterior end of the first anchoring eyelet; and
   wherein the second end of the cord body is directly attached to an exterior end of the second anchoring eyelet.

11. The device as recited in claim 10,
   wherein the additional anchoring eyelet comprises a through hole; and
   wherein the cord body divides the through hole of the additional anchoring eyelet into an upper portion and a lower portion opposite the upper portion.

12. The device as recited in claim 1, wherein the indwelling Foley catheter comprises
   a balloon port; and
   a balloon inflated through the balloon port;
   wherein the balloon keeps the indwelling Foley catheter in place;
   wherein the first anchoring eyelet is positioned on a first side of the balloon;

wherein the second anchoring eyelet is positioned on a second side of the balloon; and wherein the second side is opposite to the first side.

13. The device as recited in claim 1, wherein the cord body, the first anchoring eyelet, and the second anchoring eyelet are made of a same flexible non-stretch material; and wherein the cord body, the first anchoring eyelet, and the second anchoring eyelet are made from braided polymers.

14. A device to be placed in an indwelling Foley catheter, the device comprising a cord body;

a first anchoring eyelet attached to a first end of the cord body; and a second anchoring eyelet attached to a second end of the cord body;

wherein the second end of the cord body is opposite to the first end of the cord body;

wherein the first anchoring eyelet comprises a through hole having an axis;

wherein the second anchoring eyelet comprises a through hole having an axis;

wherein the axis of the through hole of the first anchoring eyelet is perpendicular to a length of cord body; and wherein the axis of the through hole of the second anchoring eyelet is perpendicular to the length of the cord body.

15. The device as recited in claim 14 further comprising an additional anchoring eyelet attached to a middle portion of the cord body;

wherein the additional anchoring eyelet comprises a through hole; and wherein the cord body divides the through hole of the additional anchoring eyelet into an upper portion and a lower portion opposite the upper portion.

16. A device to be placed in a catheter, the device comprising a cord body;

a first eyelet attached to a first end of the cord body; and a second eyelet attached to a second end of the cord body;

wherein the second end of the cord body is opposite to the first end of the cord body;

wherein a length of the cord body is shorter than a distance between a centroid of the first eyelet and a centroid of the second eyelet;

wherein the first eyelet comprises a through hole; and wherein the second eyelet comprises a through hole.

17. The device as recited in claim 16, wherein the through hole of the first eyelet is a straight through hole extending from a first side of the first eyelet to a second side of the first eyelet opposite the first side of the first eyelet; and wherein the through hole of the second eyelet is a straight through hole extending from a first side of the second eyelet to a second side of the second eyelet opposite the first side of the second eyelet.

18. The device as recited in claim 16, wherein the first end of the cord body is directly attached to an exterior end of the first eyelet; and wherein the second end of the cord body is directly attached to an exterior end of the second eyelet.

* * * * *